(12) United States Patent
LePivert

(10) Patent No.: US 6,235,018 B1
(45) Date of Patent: May 22, 2001

(54) METHOD AND APPARATUS FOR MONITORING CRYOSURGICAL OPERATIONS

(75) Inventor: Patrick J. M. LePivert, Jupiter, FL (US)

(73) Assignee: Cryoflex, Inc., West Palm Beach, FL (US)

( * ) Notice: Subject to any disclaimer, the term of this patent is extended or adjusted under 35 U.S.C. 154(b) by 0 days.

(21) Appl. No.: 09/429,810

(22) Filed: Oct. 29, 1999

(51) Int. Cl.$^7$ .................................................. A61B 18/18
(52) U.S. Cl. .............................. 606/20; 606/21; 600/547
(58) Field of Search ..................... 606/20–26; 600/547

(56) References Cited

U.S. PATENT DOCUMENTS

| | | | |
|---|---|---|---|
| 3,598,111 | * 8/1971 | Kahn . | |
| 3,948,269 | 4/1976 | Zimmer | 128/303.1 |
| 4,140,109 | 2/1979 | Savic et al. | 128/2.1 Z |
| 4,200,104 | * 4/1980 | Harris . | |
| 4,252,130 | 2/1981 | Le Pivert | 18/734 |
| 4,306,568 | 12/1981 | Torre | 128/734 |
| 4,483,341 | 11/1984 | Witteles | 128/402 |
| 4,946,460 | 8/1990 | Merry et al. | 606/24 |
| 5,069,223 | 12/1991 | McRae | 128/734 |
| 5,334,181 | 8/1994 | Rubinsky et al. | 606/22 |
| 5,341,807 | * 8/1994 | Nardella . | |
| 5,433,717 | 7/1995 | Rubinsky et al. | 606/20 |
| 5,706,810 | 1/1998 | Rubinsky et al. | 128/653.1 |
| 5,759,159 | * 6/1998 | Masreliez | 600/547 |
| 5,916,212 | 6/1999 | Baust et al. | 606/22 |

* cited by examiner

Primary Examiner—Michael Peffley
Assistant Examiner—Roy Gibson
(74) Attorney, Agent, or Firm—McHale & Slavin

(57) ABSTRACT

A method and system for monitoring the progress of an ice ball produced by a cryoprobe during a surgical procedure measures the complex impedance of the ice ball. An electrical model of the zones in the ice ball is employed to calculate the size of the zones using the complex impedance measurements. The ice ball zones are displayed to assist the surgeon in controlling the cryoprocedure.

19 Claims, 5 Drawing Sheets

METHOD AND APPARATUS FOR MONITORING CRYOSURGICAL OPERATIONS

BACKGROUND OF THE INVENTION

The field of the invention is the measurement of the effects on tissue during cryosurgical operations, and more particularly, the depiction of frozen tissue during such operations.

The primary use of cryosurgery is to ablate tissue in situ by the application of extreme cold to the tissue. Cell death results and the dead cells typically slough. This process is referred to as "cryonecrosis". The use of cryonecrosis procedures has distinct advantages over other surgical methods including: little or no bleeding; lessened need for anesthesia; faster recovery time; lack of scarring; and preservation or selective alteration of structural components of tissue such as collagen. The cryonecrosis procedures lend themselves well to minimally invasive surgery such as percutaneous, endoscopic, and endovascular surgery. They also can be performed more frequently on an out-patient basis, and can be performed on high-risk patients who could not withstand traditional surgery.

Cell death is achieved in cryosurgery through the removal of heat by application of extremely cold temperature, either directly to the tissue, as in the application of a swab or spray of liquid nitrogen to the skin, or through contact with a very cold instrument, the "cryoprobe". Cryoprobes such as those described in U.S. Pat. Nos. 4,946,460; 348,369; 5,334,181; 5,916,212; 4,483,341, typically are powered by liquid or gaseous coolants or a mixture of both. In a typical application, nitrous oxide is delivered to an expansion chamber within the tip of the cryoprobe, where extremely cold temperatures result from the Joule-Thompson effect. The cold temperatures spread to the tip and then to the surrounding tissue.

Heat is extracted from the surrounding tissue in a "heat sink" effect. The tissues freeze first at the surface of the cryoprobe, and an "ice ball" of frozen tissues grows outward from the cryoprobe surface as the heat is extracted. Although this ice ball may be seen, either with the eyes or through medical imaging systems, the boundaries of the ice ball do not accurately measure the region of cryonecrosis. A longstanding problem in this art is the accurate detection and depiction of cell death so that the surgeon can control the cryonecrosis procedure.

The measurement of tissue temperature (thermometry) is an accepted method of predicting cryonecrosis. However, thermometry has severe shortcomings. The cryonecrotic range of temperature is wide, imprecise, and variable from tissue to tissue. It is well known that cryonecrosis can occur at temperatures considered as non-lethal. On the other hand, some tissues are very cryoresistant. Due to this uncertainty, "overkill" is usually built into cryosurgical procedures. The usual recommendations for a standard destructive cryosurgical application, when addressing a cancerous lesion for example, are quick freezing, slow thawing, and repetition of this freezing/thawing cycle until a tissue temperature at least −40 degrees Celsius is measured at the lesion boundary. When this is done, the visible ice ball extends well beyond the boundary of the lesion. Furthermore, tissular thermometry is an invasive method, requiring the insertion of measuring devices, usually in the form of thermocouple needles. The cryoprobe itself provides no information on the temperature of the surrounding tissue and temperature measurements provide only point-specific information. Methods such as those described in U.S. Pat. Nos. 5,433,717 and 5,706,810 have been proposed for producing temperature maps using magnetic resonance imaging (MRI) systems, but such methods are very expensive due to the high cost of the MRI system.

Other methods have also been proposed for predicting cryonecrosis, but all of these image the boundary of the ice ball and do not detect the region inside the ice ball where cell death actually occurs. Such known methods as heat flux measurements, CAT scanning, sonography, therefore exaggerate the boundary in which cell death occurs.

Another such method is bioelectrical impedancemetry which measures the electrical impedance of the ice ball. Close correlations have been found between the impedance of the ice ball and the cryodestructive tissue temperatures. As described in U.S. Pat. No. 4,252,130, when a certain amount of heat is extracted from a biological system, there is a change of phase or change of state which converts the freezable water into ice and has the result of "extracting" from the cell the water of solvation and the "structural" water, in particular the membranous water. Since the stability of a biological system is dependent on the maintenance of an exact concentration of aqueous solutions, the consequences of the loss of water in the crystalline structure of newly formed ice is substantial.

Impedancemetry or bioelectrical tissue impedance measurement detects the moment water freezes as an increase in electrical impedance of the tissue. At least two electrodes are employed to measure the impedance across the target tissues (e.g. a tumor) and to provide an indication to the surgeon when that impedance suddenly increases. Such prior impedancemetry methods have some of the shortcomings of thermometry in that their ability to accurately predict cryonecrosis was limited. In addition, as exemplified by U.S. Pat. Nos. 4,140,109 and 4,306,568 many prior procedures are invasive in that they require the implantation of separate needle electrodes or other sensors.

SUMMARY OF THE INVENTION

The present invention is a method and apparatus for measuring ice ball production and growth in a biological medium such as tissue during a freezing procedure such as cryosurgery. More particularly an electrical model of the ice ball is established which relates the size of its eutectic zone to its complex impedance, the complex impedance of the ice ball is measured during the freezing procedure, the size of the eutectic zone is calculated using the electrical model and the measured complex impedance, and the size of the calculated eutectic zone is visually indicated.

The present invention enables one to image in real-time the growth of the ice ball and the eutectic freezing zone around a cryoprobe or a sensor in contact with the target tissue, during a cryosurgical procedure. As a result, one can predict the area of tissue destruction, in both surface as well as in depth, around the cryoprobe. The surgeon can thus control manually or with computer assistance the necessary power and duration of a cryosurgical application to achieve a precise and selected destructive area around one or more cryoprobes.

The present invention also enables the surgeon to visualize and to control the operation in locations where it is difficult or even impossible to see the ice ball (e.g., endoscopy, minimally invasive surgery, endovascular surgery). An image of the forming ice ball is produced on a monitor and may be registered with a previously acquired anatomic image or anatomic images acquired during the operation using ultrasound, x-ray CT or MRI systems.

There are situations when more than one cryoprobe is used, for example, an irregularly shaped and/or large lesion. In such instances, several cryoprobes must be used to cover the entire volume with overlapping ice balls. These probes work simultaneously for cumulative heat sink effects and to expedite the procedure.

In such procedures, each cryoprobe develops an ice ball towards the outer margin of the lesion until it encompasses the lesion while simultaneously tending to grow inwardly to overlap the margins of the other expanding ice balls. However, it is more important to monitor the change of phase at the margin of the lesion because it is the region where the lesion usually grows and where the vasculature supports its expansion. Also, the amount of healthy tissue destroyed, outside the lesion, should be kept to a minimum.

Up to 12 microcryoprobes, or even more, can be used to better match the multiple ice ball shape and volume to the lesion shape and volume. Each probe is equipped with electrical connections and sensors to record data necessary to construct and display, in real time, the image of the destructive area and the sub eutectic area. Each probe is located in the lesion under direct visualization or image guidance (CT, ultrasound, or MR) at an optimal distance from the other, whenever possible. This distance is derived from the specifications referring to its power, stated as the ability to change the phase of a certain volume of a standard electrow conductive biological medium, i.e., saline solution, in a designated time.

Since the freezing process is slow in these large and/or irregularly shaped lesions, in the nature of 5 minutes to 20 minutes, it is possible to use a dispatching apparatus. Such a dispatcher permits automatic recording, e.g., at intervals of 0.25 or 0.5 second, the data at each electrode/cryoprobe. This data is continuously collected to construct an image of the destruction based on the spatial relationship of the probes to each other.

The invention may also be integrated into a complete computer aided operation. The invention may be used for the purpose of simulation of different operative conditions, in order to train and guide surgeons. The registered computerized images provided by the invention may be compared with the pre or per operative images of the lesion, and the information used to control the placement and operation of the cryoprobe.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

During cryosurgery, "freezing", i.e., crystallization of tissue, results from the creation of temperature gradients in the tissue, due to the extraction of heat by the cryoprobe. The crystallization is observed in various intratissular fluids. These include the intracellular fluid (within the cells); the extracelluar fluid (between the cells); and the vascular fluid (consisting of the microvasculature of the tissue). At any point in time, the zone around a cryoprobe can be characterized by the zones in which complete ("eutectic") and incomplete ("pre-eutectic") freezing has occurred with respect to these fluids. We sometimes refer to eutectic freezing as "dry ice" and pre-eutectic freezing as "wet ice".

Figure 1:
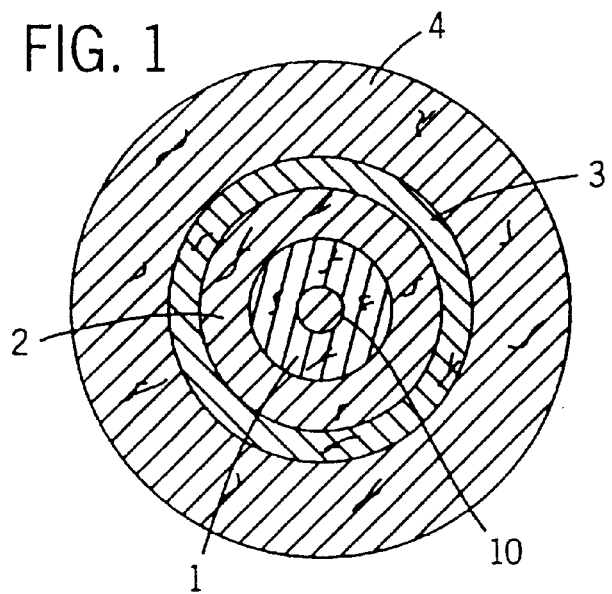
FIG. 1 is a schematic representation of an ice ball produced in tissue by a cryosurgical procedure.

The different zones in an ice ball produced in tissues are depicted schematically in FIG. 1. In this example, cold is applied with a probe 10 in the center of the ice ball. A first region 1 at the center indicates the zone in which complete intracellular crystallization has occurred. A surrounding second region 2 indicates the extent of incomplete intracellular crystallization and the region contained within zones 1 and 2 has complete extracellular crystallization. The next region 3 indicates a surrounding zone in which incomplete extracellular crystallization occurs and the outer boundary of this zone 3 is the visible ice front. And finally, a fourth region 4 is a zone in which tissue temperature is lowered (i.e. hypothermia).

We have discovered that eutectic freezing of the extracellular fluids includes eutectic freezing of the vascular fluids. We also have discovered that eutectic freezing of the vascular fluids results in thrombosis ("cryothrombosis") of the microvasculature. Finally, we have determined that thrombosis of the microvasculature results in cell necrosis within a matter of hours. We have concluded, therefore, that eutectic freezing of the extracellular fluids is predictive of cryonecrosis and a measurement of extracellular fluid eutectic freezing is a measurement of the extent of cryonecrosis.

Figure 2:
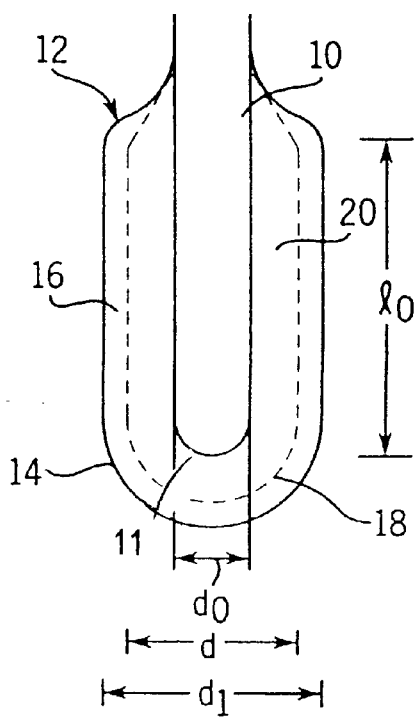
FIG. 2 is a schematic representation of an ice ball formed around a cryoprobe.

From these discoveries, a "two phase" physical model can be constructed, showing the geometric form of the boundary of the ice ball, and the boundary of the region of complete extracellular crystallization. FIG. 2 illustrates this model, where a cylindrical cryoprobe 10 having a hemispherical tip 11 produces an ice ball 12 in the tissues which surround it. The boundary 14 of the ice ball 12 is the outer boundary of a pre-eutectic zone 16 where extracellular fluids are partially frozen. A boundary 18 hidden inside the ice ball 12 defines the outer boundary of the eutectic zone 20 where complete extracellular freezing and delayed cell death occur. The present invention measures and displays this eutectic zone boundary so that the destructive cryogenic procedure can be accurately controlled.

The measurement of ice ball formation is performed using an improved bioeletrical impedance measurement method. Biological tissue behaves as an electrolyte that can be characterized in terms of its resistance and capacitance. It is well known that the resistance of tissue increases when it is frozen. The same is true with the alternating impedance of tissues, at least when measured at relatively low frequencies, for example, from 500 to 5000 Hertz by applying known currents and measuring the resulting potentials or by applying known voltages and measuring the resulting currents.

Thus, measuring impedance modulus in a biological medium or tissue has been proven valuable in detecting eutectic crystallization. But this measure when obtained through needle electrodes or through cryoprobes inserted into the tissue is not able to give the operator a precise appreciation of the growing eutectic zone inside the ice ball.

To practice the present invention an electrical model of the ice ball is presented which relates the dimensions of its eutectic zone to its electrical characteristics. The electrical characteristics are then measured using a properly placed sensing electrode and a remotely located electrode. The complex impedance is measured between these two electrodes at one or more frequencies, and from these measurements and the electrical model the dimensions of the eutectic zone within the ice ball can be calculated.

Figure 3:
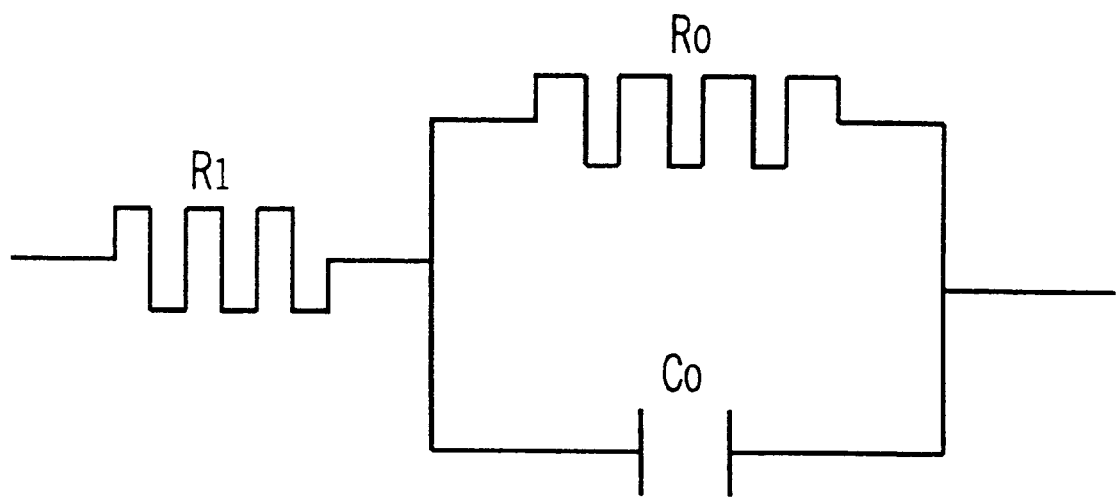
FIG. 3 is an electrical model of the ice ball depicted in FIG. 2.

Referring particularly to FIGS. 2 and 3, one preferred electrical model of the ice ball represents the eutectic zone 20 as a lumped resistance $R_0$ connected in parallel with a lumped capacitance $C_0$. The pre-eutectic zone 16 and the medium (i.e. unfrozen tissue) are modeled as a lumped resistance $R_1$ connected in series. The complex impedance Z (modulus Z, argument Z) of this model is $$|Z|\cos\theta = \frac{R_0}{1+t_0^2} + R_1 \tag{1}$$

$$|Z|\sin\theta = \frac{R_0 t_0}{1-t_0^2} \tag{2}$$

where: $t_0 = R_0 C_0 \omega$; $\omega = 2\pi f$; and f=frequency.

Given that in a homogenous medium $R_0 C_0 = p_0 \epsilon_0$, then $t_0 = p_0 \epsilon_0 \omega$, where $\epsilon_0$ is the susceptibility and $p_0$ is the resistivity of the medium. The value of $R_0$ can thus be computed, and from this value one can calculate the eutectic zone dimensions using formulas that relate the eutectic zone shape that is produced by the particular probe that is used.

$$R_0 |Z| \sin\theta \left( \frac{1+t_0^2}{t_0} \right) \tag{3}$$

$$R_1 = |Z| \left[ \cos\theta - \frac{\sin\theta}{t_0} \right] \tag{4}$$

For example, when using the cylindrical, closed-end cryoprobe 10 having diameter $d_0$ the assumption is made that the boundaries 14 and 18 of the zones 20 and 16 are cylindrical along the length $l_0$ of the cooling/electrode portion of the cryoprobe 10, and they are hemispherical over the end of the cryoprobe 10. The electrical susceptibility of tissues in the eutectic zone 20 is $\epsilon_0$ and its resistivity is $p_0$. The equation relating the calculated resistance $R_0$ to the diameter (d) of the eutectic zone boundary 18 is as follows:

$$1/R_0 = 2\pi/p_0[l_0/\log_n(d/d_0) + d_0/2(1-d_0/d)] \tag{5}$$

The susceptibility and resistivity values $\epsilon_0$, and $p_0$ are given the following experimentally determined initial values:

$\epsilon_0 = 2 \times 10^{-11}$ farad/cm $p_0 = 8 \times 10^7$ ohm cm.

Variations in these values may occur over time due to changes in the temperature and crystalline structure of the frozen medium. It is a further aspect of the present invention that the measurement of complex impedance at several frequencies enables the calculation of $t_0(\omega)$ resulting in a better determination of the eutectic zone dimensions. After measurement at two frequencies, $\omega$ and $\omega'$, $p_0 \epsilon_0$ is calculated as follows:

$$p_0\varepsilon_0 = \frac{t_0(\omega)}{\omega} \sqrt{\frac{Z(\omega')\sin\theta(\omega') - Z(\omega)\sin\theta(\omega)}{Z(\omega)\sin\theta(\omega) - \frac{\omega'}{\omega}Z(\omega')\sin\theta(\omega')}} \tag{6}$$

This value is thus continuously measured and updated throughout the measurement procedure to improve the accuracy of the calculations in equations (3) and (4).

Other electrical models are possible and the calculations relating the electrical model to ice ball dimensions will also differ as a function of cryoprobe shape. For example, the pre-eutectic zone 16 and the medium may also be modeled as a resistance element $R_1$ connected in parallel with a capacitance element $C_1$. The cryoprobe end 10 may be flat rather than hemispherical or it may be an open sleeve that cools at its distal end.

Figure 4:
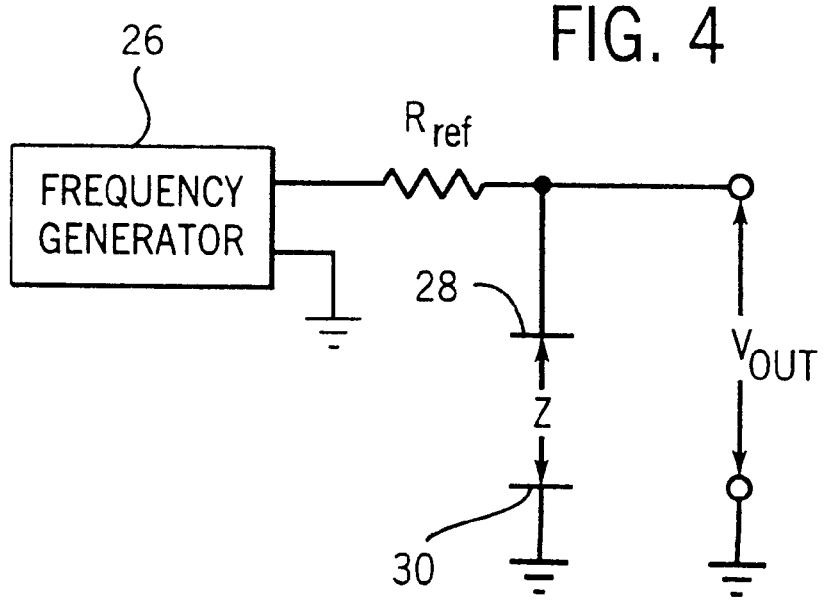
FIG. 4 is a circuit diagram of a complex impedance measurement system.

To monitor the growing eutectic zone the electrical impedance is repeatedly measured during the cryosurgical procedure. Referring to FIG. 4, the measurements are made with a frequency generator 26 which produces a sinusoidal voltage of amplitude $A_{ref}$ and phase $\phi_{ref}$ at the chosen frequency f. This voltage is applied through a known resistor $R_{ref}$ to an electrode 28 on the cryoprobe 10 and circuit ground is connected to a remote electrode 30. The voltage $V_{OUT}$ is measured across the electrical impedance Z between the two electrodes 28 and 30. The relative amplitude $A_{OUT} = V_{OUT}/A_{ref}$ of the measured output voltage $V_{OUT}$ as well as its phase ($\phi_{OUT}$) are determined and used to calculate the complex values of the impedance Z.

$$Z_{magnitude} = |Z| = R_{ref} A_{out}(1 + A^{out2} - 2A_{out}\cos\phi_{out})^{1/2} \tag{7}$$

$$Z_{angle} = \theta = \text{Arctan}[\sin\phi_{out}(A_{out} - \cos\phi_{out})^{-1}] \tag{8}$$

The complex values of the impedance can be measured at a number of frequencies, and the resistance $R_1$ of the pre-eutectic zone 16 and the resistance $R_0$ and capacitance $C_0$ of the eutectic zone 20 are calculated using equations (3) and (4) and:

$$C_0 = t_0/R_0\omega \tag{9}$$

The dimension of the eutectic zone is then calculated using equation (5) and the results displayed.

DESCRIPTION OF THE PREFERRED EMBODIMENTS

Figure 5:
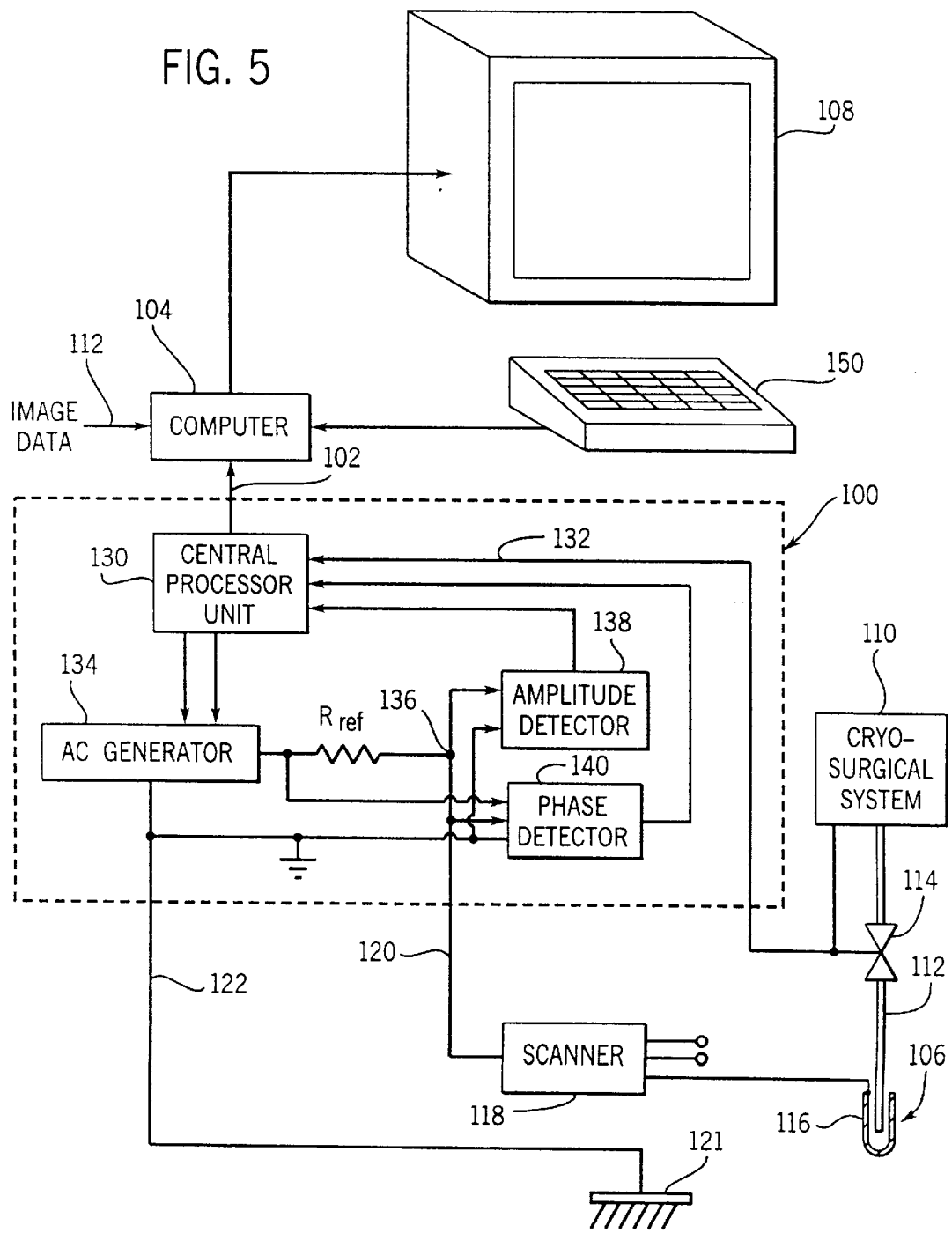
FIG. 5 is a block diagram of a preferred cryosurgical monitor system which employs the present invention.

Referring particularly to FIG. 5, a system for monitoring a cryosurgical operation includes an impedance measurement unit 100 that produces an impedance signal at output 102 for a computer 104. The computer 104 is programmed to process the impedance signals as will be described in more detail below to calculate the dimensions of the ice ball produced around the tip of a cryoprobe 106. These dimensions are used to produce an image on display 108 that may be viewed by the surgeon and used to control the operation of a cryosurgical system 110. In the preferred embodiment computer 104 receives real-time digital image data at input 102 which depicts the anatomy being treated. Such image data may be produced, for example, by an x-ray CT, ultrasonic or MR imaging system (not shown in the drawings) that delivers fully reconstructed 2D images at a desired frame rate. These images also contain markers that locate the freezing tip of the probe 106 therein, and the computer 104 produces an image of the eutectic zone that is registered on the displayed anatomic image using these markers. The image of the eutectic zone is sized in response to the impedance data received from the impedance processor 100 and it grows in real time as the cryosurgical procedure progresses. The image of the eutectic zone may overlay the anatomical image, or it may be blended therewith to become semitransparent so that the underlying anatomy (e.g. tumor) can still be seen.

The cryosurgical system 110 may be any one of a number of commercially available systems such as that disclosed for example in U.S. Pat. No. 5,334,181. The system 110 provides a cold cryogenic liquid that flows through a duct 112 to the cryogenic probe 106 when a valve 114 is opened in response to a trigger signal manually initiated by the surgeon. The cryogenic fluid flows out the end of the duct 112 and cools the tip of the probe 106.

The conductive material of the cooled tip of the cryogenic probe 106 is a sensing electrode 116 that is in intimate contact with the surrounding tissues from which heat is extracted. This sensing electrode 116 is electrically connected to one input of a scanner 118 that selects one of three such input signals and applies it to through line 120 to the impedance processor 100. The scanner 118 enables up to three sensing electrodes 116 to be monitored during the procedure.

A remote electrode 121 also connects to the impedance processor 100 through line 122. The remote electrode is attached to the skin of the patient being treated and makes good electrical connection therewith. AC current flowing between the sensing electrode 116 and the remote electrode 121 flows through the ice ball being formed at the tip of the cryogenic probe 106. Impedance changes in the ice ball affect both the magnitude and phase of this current and it is these changes that are measured and processed by the impedance processor 100.

The impedance processor 100 is operated by a central processor unit 130 when it receives a signal through input line 132 indicating that cryogenic cooling has been triggered by the surgeon. The CPU 130 operates an AC generator 134 which produces a sinusoidal output voltage of amplitude A and frequency f. Both the amplitude A and frequency f can be changed by the CPU 130 to carry out different measurement sequences. The AC voltage produced by generator 134 produces a current that flows in a loop which includes a reference resistor $R_{ref}$, the electrodes 116 and 121, and the tissues there between. These tissues include the ice ball.

A voltage $V_{OUT}$ is produced by the AC current flowing through the ice ball at a node 136. This voltage is applied to the inputs of an amplitude detector 138 and a phase detector 140. The amplitude detector 138 includes two components which are well known to those skilled in the art. The first component is a peak detector circuit which produces an analog signal level equal to the peak amplitude $A_{OUT}$ of the voltage $V_{OUT}$. The second component is an analog-to-digital converter which digitizes this peak amplitude $A_{OUT}$ and inputs the digitized value to the CPU 130. The phase detector 140 is also a well known circuit which produces a digital number $\phi_{OUT}$ indicative of the difference in phase between the signal $V_{ref}$ output by AC generator 134 and the signal $V_{OUT}$ at the node 136. This is accomplished by detecting the successive zero crossings of each signal and incrementing a counter during the interval between zero crossings to measure the phase difference.

The central processor unit 130 is programmed to continuously measure the complex impedance of the ice ball and output the measurements to the computer 104. This is accomplished using the $A_{OUT}$ and $\phi_{OUT}$ values produced by the detectors 138 and 140 and equations (7) and (8) discussed above. During surgery, the CPU 130 produces a stream of impedance modulus values (i.e. $Z_{magnitude}$) and argument values (i.e. $Z_{angle}$).

In addition to managing the display 108 as described above, the computer 104 is programmed to process the complex impedance values received from processor 100 and calculate the size of the eutectic zone using equations (3) and (5). In addition, in the multifrequency mode, computer 104 updates the value of the product $p_0\epsilon_0$ as described above.

Figure 9:
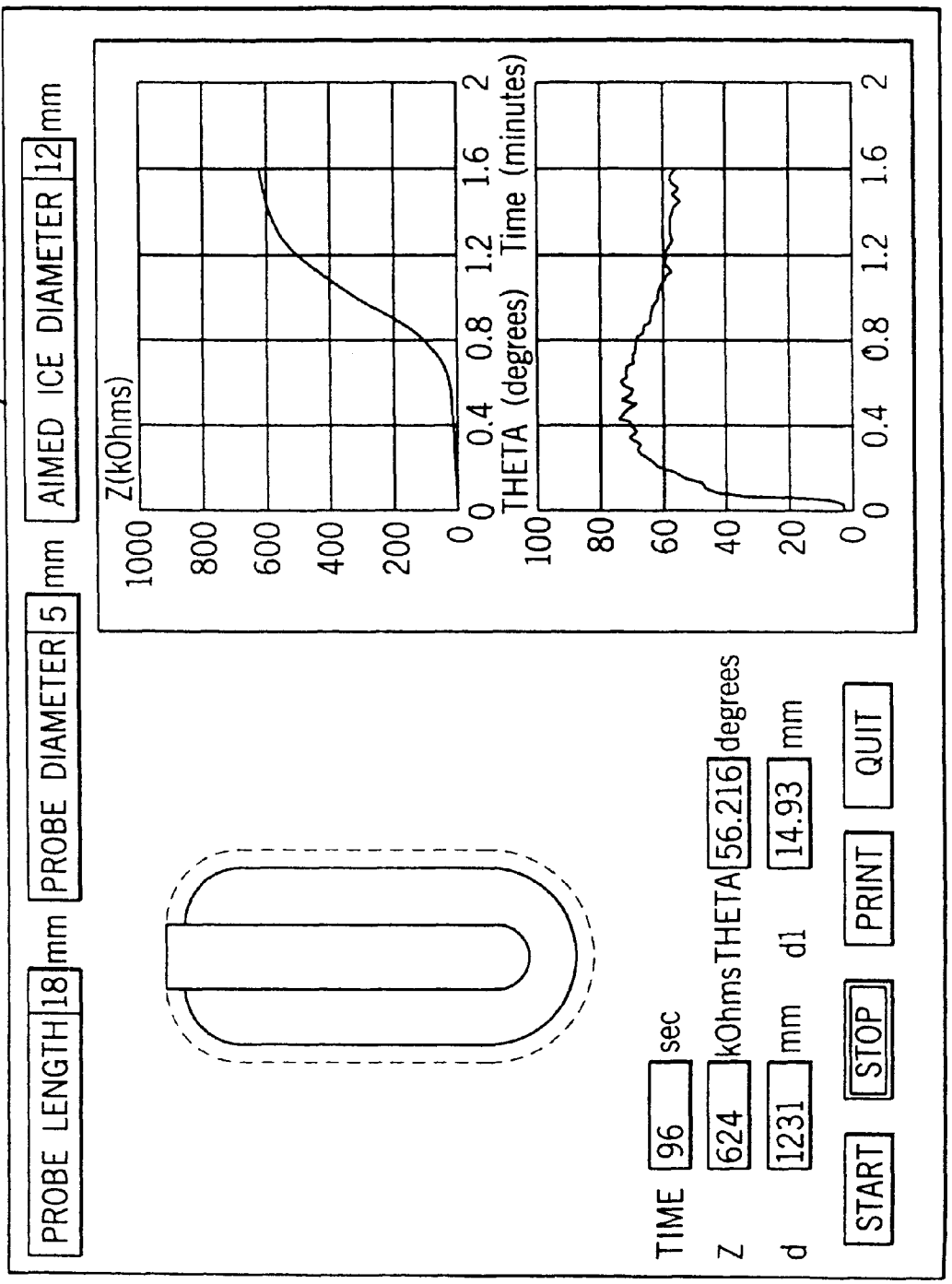
FIG. 9 is a pictorial representation of one embodiment of the information displayed on a monitor which forms part of the system of FIG. 5.

As described above, the computer 104 preferably produces an image of a properly sized eutectic zone and registers it with an anatomic image of the patient lesion. If the latter is not available or desirable, the ice ball image and other monitored parameters may be displayed on the monitor 108 as shown in FIG. 9. The graphs on the right, are the history of the impedance modulus and argument. The two-dimensional image is the ice ball (eutectic and pre-eutectic) calculated in real time from these values. The freezing depth and diameter are given in millimeters. The limits of destructive freezing estimated and required by the operator appear before initiation of cooling when the cryoprobe is in proper position in the tissue. Thus, during the cryoapplication the operator visualizes the progression of the destructive ice front. He can control the therapeutic efficiency of the cryoprobe through the rate of growth of the ice ball or through the impedance modulus curve. Also, the probe parameters (size, shape, and length of insertion in the tissue) have been entered.

There are many alternative embodiments of the invention. In the preferred embodiment described above the sensing electrode 116 is an integral part of the cryoprobe 106 and wraps around its cooling tip. In such case the cooling tip is placed within the tissue to be cooled and is fabricated from a conductive metal such as stainless steel which is biocompatible. Other conductive metals may also be used if they are coated with a biocompatible metal such as gold, silver or titanium. Three different structures for such a cryoprobe 106 are shown in FIGS. 6, 7 and 8.

Figure 6:
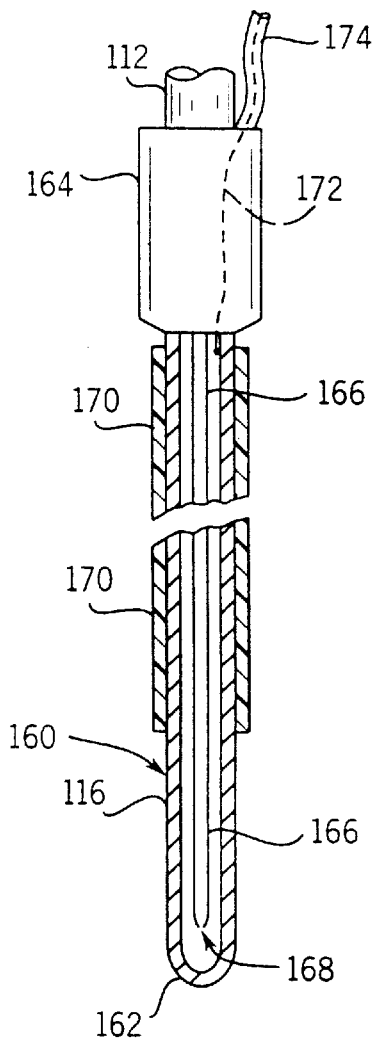
FIGS. 6, 7 and 8 are cross sectional views of three preferred cryoprobes for use in the system of FIG. 5.

Referring particularly to FIG. 6, one embodiment of the cryoprobe with integral sensing electrode includes a stainless steel tubular shaft 160 that is rounded at its distal end 162 and has a handle 164 at its proximal end. An inner tube 166 delivers cryogenic fluid to the distal end 162 where it exits through an opening 168 and vaporizes to cool the metallic shaft 160. The shaft 160 is inserted into tissue to be treated and its exposed outer surface is in intimate contact with the tissues to conduct heat away from them and produce a surrounding ice ball.

An insulating sleeve 170 surrounds the shaft 160 and extends from the handle 164 to a location near the tip 162. The sleeve 170 is preferably made of an insulating material such as that sold under the trademark Teflon. The sleeve 170 leaves exposed a length of the shaft 160 corresponding to the size of the region being treated. The center lead 172 in a coaxial cable 174 connects to the proximal end of the shaft 160, and an electrical connection is thus established with the tissues in contact with the exposed outer surface of the shaft 160. The cable 174 connects to the scanner 118 (FIG. 5). The exposed outer surface of the shaft 160 thus defines the volumetric surface of the sensing element 116 and it is the same surface employed to transfer heat from the surrounding ice ball.

Figure 7:
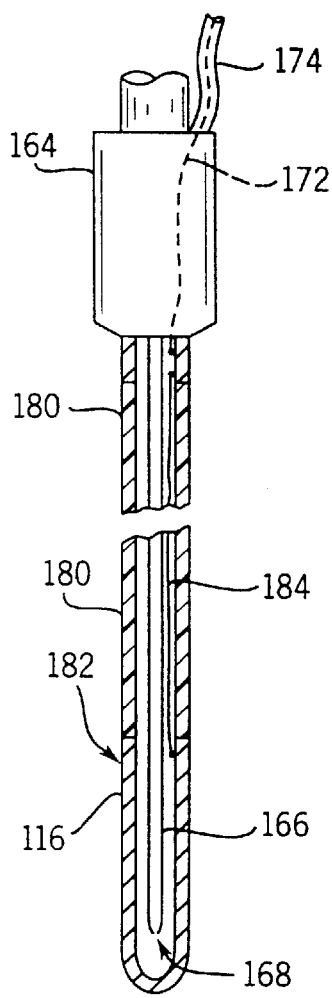
Figure 8:
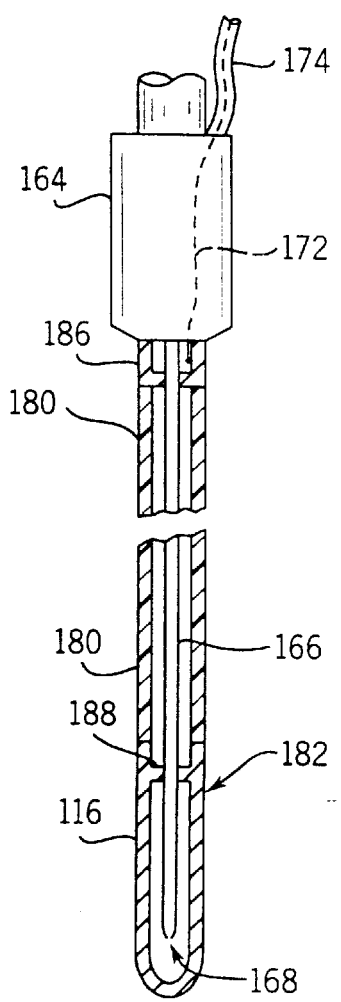

A second embodiment shown in FIG. 7 has many of the same elements as the first embodiment. In this embodiment the metallic shaft is replaced with a non-conductive flexible shaft 180 that connects the handle 164 to a stainless steel conductive tip 182. Non-conductive materials such as polypropylene, polyethylene, or polyamide may be used. Electrical connection is established between the center lead 172 and this conductive tip 182 by an inner wire 184 that extends along the length of the flexible non-conductive shaft 180 in the annular space between it and the inner tube 166.

A third embodiment shown in FIG. 8 is very similar in construction to the embodiment in FIG. 7. Instead of the inner wire 184, however, the inner tube 166 is used as an electrical conductor between the conductive tip 182 and the center lead 172. To establish electrical connection, an electrical connector 186 is soldered to the inner tubel 66 near its handle end, and a conductive annular bridge 188 is soldered in place to connect the inner tube 166 to the conductive tip 182.

The sensing element 116 need not be an integral part of the cryogenic probe. For example, the sensing element 166 may take the form of a ring or a truncated cone that is placed in contact with the surface of tissue to be cryogenically treated with a spray coolant. The surface of the ring provides electrical contact with the tissues being treated over a surface that is substantially coextensive with the surface through with heat is extracted from the tissue. Regardless of the shape of the sensing electrode 116, the important consideration is that current flowing between the sensing electrode 116 and the remote electrode 121 pass through the ice ball produced by the cooling device in such a manner that the current is affected by the growth of the ice ball.

What is claimed is:

1. A method for monitoring the progress of a cryoprocedure, the steps comprising:
   (a) establishing an electrical model of an ice ball produced by the cryoprocedure which relates the size of a eutectic zone therein to the complex impedance of the ice ball;
   (b) measuring the complex impedance of the ice ball during the cryoprocedure;
   (c) calculating the size of the eutectic zone using the measured complex impedance and the electrical model; and
   (d) displaying an indication of the eutectic zone size.

2. The method as recited in claim 1 in which the cryoprocedure is performed on tissue using a cryoprobe.

3. The method as recited in claim 2 in which the complex impedance is measured by:
   placing a sensing electrode in electrical contact with the tissue;
   placing a remote electrode at another location remote from the tissue;
   applying an alternating voltage across the two electrodes such that a current flows through the tissue.

4. The method as recited in claim 3 in which the complex impedance is measured by detecting the amplitude and phase of the current lowing through the tissues.

5. The method as recited in claim 1 in which the electrical model includes an impedance model of the eutectic zone in an ice ball and an impedance model of a pre-eutectic zone in the ice ball.

6. The method as recited in claim 5 which includes:
   calculating the size of the pre-eutectic zone using the measured complex impedance and the electrical model; and
   displaying an indication of the pre-eutectic zone size.

7. The method as recited in claim 1 in which the eutectic zone size is displayed by producing an image of an ice ball on a monitor and indicating the size of the eutectic zone therein.

8. The method as recited in claim 7 in which steps b) and c) are repeated continuously during the cryoprocedure and the size of the eutectic zone is displayed as a boundary in the ice ball image which changes location.

9. The method as recited in claim 7 in which the cryoprocedure is performed on tissues and it further includes:
   e) acquiring the anatomic image of the tissues; and
   f) registering the anatomic image with the ice ball image on the monitor to depict the ice ball image at the location in the tissues being treated by the cryoprocedure.

10. System for monitoring a cryoprocedure performed on tissue, the combination comprising:
    a sensing electrode having a conductive surface in electrical contact with the tissue;
    a remote electrode connected to conduct current passing through the tissue and the sensing electrode;
    an impedance processor having inputs connected to the sensing electrode and the remote electrode and being operable to produce an alternating current through the tissue and measure the complex electrical impedance thereof;
    in which said impedance processor includes;
    a generator which produces the alternating current;
    an amplitude detector which measures the voltage between the two electrodes;
    a phase detector which measures the phase of the voltage between the two electrodes; and
    computer means connected to receive the measured electrical impedance from the impedance processor and being operable to produce an indication of the eutectic boundary of an ice ball formed in the tissue by the cryoprocedure.

11. The system as recited in claim 10 in which the sensing electrode forms part of a cryoprobe which extracts heat from the tissue to produce the ice ball.

12. The system as recited in claim 11 in which the conductive surface of the sensing electrode is substantially coextensive with a surface of the cryoprobe through which said heat is extracted.

13. The system as recited in claim 10 in which the impedance processor produces complex impedance measurements repeatedly during the cryoprocedure and the computer means produces a real-time indication of the growth of the eutectic boundary in the ice ball during the cryoprocedure.

14. The system as recited in claim 10 in which the computer means includes a monitor that depicts the ice ball and indicates the location of said eutectic boundary.

15. The system as recited in claim 14 in which the monitor depicts a graph indicating a series of complex impedance measurements made during the cryoprocedure.

16. The system as recited in claim 15 in which the magnitude and phase of the measured impedance is depicted.

17. The system as recited in claim 14 which includes means for producing an anatomic image of the tissues and the anatomic image is depicted on the monitor in registry with the depiction of the ice ball.

18. The system as recited in claim 10 in which the computer means includes a stored model which relates measured complex impedance to the size of a eutectic zone in the ice ball.

19. The system as recited in claim 18 in which the stored model also relates measured complex impedance to the size of a pre-eutectic zone in the ice ball, and the computer means is also operable to produce an indication of the boundary of the pre-eutectic zone.

\* \* \* \* \*